United States Patent [19]

Corvi Mora

[11] Patent Number: 4,672,055
[45] Date of Patent: Jun. 9, 1987

[54] ERYTHROMYCIN SALT WITH MUCOSECRETOLYTIC AND FLUIDIZING ACTIVITY AND PHARMACEUTICAL COMPOSITIONS THEREOF

[75] Inventor: Camillo Corvi Mora, Piacenza, Italy

[73] Assignee: Camillo Corvi S.p.A., Italy

[21] Appl. No.: 711,662

[22] Filed: Mar. 14, 1985

[30] Foreign Application Priority Data

Apr. 2, 1984 [IT] Italy ................... 20354 A/84

[51] Int. Cl.$^4$ ............... A61K 31/71; C07H 17/08
[52] U.S. Cl. ............................ 514/29; 536/7.2
[58] Field of Search .............. 536/7.2, 7.3; 514/29

[56] References Cited

U.S. PATENT DOCUMENTS

| | | | |
|---|---|---|---|
| 2,870,138 | 1/1959 | Murray et al. | 536/7.2 |
| 4,219,641 | 8/1980 | Desposato et al. | 536/7.2 |
| 4,264,765 | 4/1981 | Bodor et al. | 536/7.2 |

FOREIGN PATENT DOCUMENTS 0096116 3/1979 European Pat. Off. .

OTHER PUBLICATIONS

Chemical Abstracts, vol. 90, No. 10, 5th Mar. 1979, p. 8, No. 80589v, "Fluorimetric Determination of Erythromycin and Erythromycin Ethylsuccinate in Serum by a High-Performance Liquid Chromatographic Post--Column . . . ".

Primary Examiner—Johnnie R. Brown
Assistant Examiner—Elli Peselev
Attorney, Agent, or Firm—Ostrolenk, Faber, Gerb & Soffen

[57] ABSTRACT

The erythromycin salt of 5-(3-carboxy-1-oxopropoxy)-α,α, 4-trimethyl-3-cyclohesene-1-methanol acid is described.

This salt shows a mucosecretolytic and fluidizing activity. There is further described a process for the preparation of said salt, as well as pharmaceutical compositions with mucosecretolytic and fluidizing action which contain the novel salt.

3 Claims, No Drawings

ERYTHROMYCIN SALT WITH MUCOSECRETOLYTIC AND FLUIDIZING ACTIVITY AND PHARMACEUTICAL COMPOSITIONS THEREOF

An object of this invention is the erythromycin salt of 5-(3-carboxy-1-oxopropoxy)-α, α 4-trimethyl-3-cyclohexene-1-methanol acid, of the formula

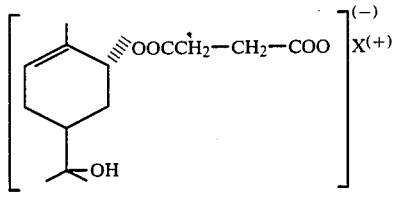

Code: (CO/1311)

where X (+) represents the monovalent catin of erythromycin and the anion is derived from 5-(3 carboxy-1oxopropoxy)-α, α4-trimethyl-3-cyclohexene-1-methanol acid having the formula

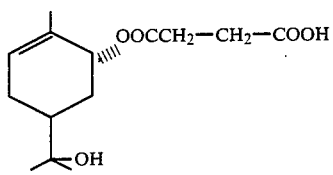

Code: (CO/1032)
$C_{14}H_{22}O_5$
mol. wt. 270.32

The product of formula II, an ester-acid, which is derived from d,1-trans-sobrerol, is a novel one and, therefore, it falls within the present invention.

The d,l-trans-sobrerol is known, however, because of its employment in the therapy of respiratory diseases, since it acts as a mucoregulator and expectorant.

It has been found, unexpectedly, that the erythromycin salt (I), beside having a mucosecretolytic and fluidizing activity greater than the one which should be attributed to sobrerol, provides a novel well-balanced antibiotic complex useful for the selective therapy of the respiratory tract.

Erythromycin, as it is known, is an antibiotic substance suitable for treating the gram-positive infections and it is particularly effective against staphylococci, streptococci, pneumococci, which are, on the contrary, resistant against the other antibiotic drugs. Erythromycin is further effective for treating infections caused by a mixture of gram-positive and gram-negative bacteria. The formula of erythromycin is given herebelow:

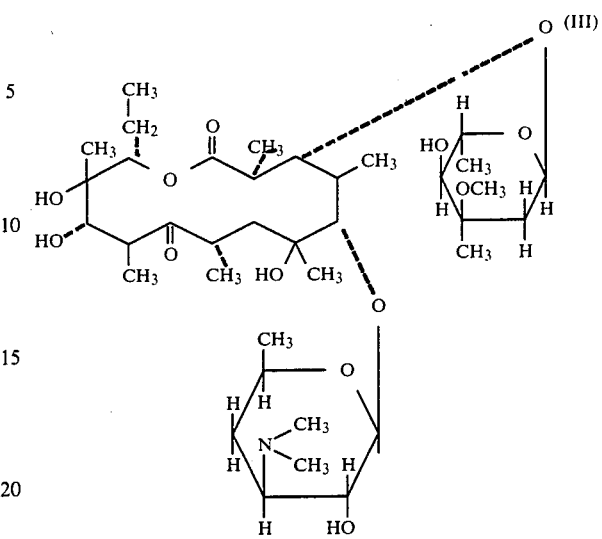

An object of the invention is, further, to provide a process for preparing the ester-acid (II) (code CO/1032) by reacting succinic anhydrine (IV) with d, 1 trans-sobrerol (V) according to the following scheme:

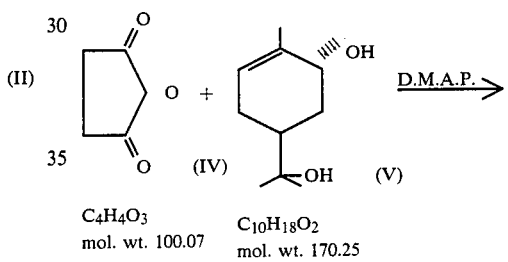

$C_4H_4O_3$
mol. wt. 100.07

$C_{10}H_{18}O_2$
mol. wt. 170.25

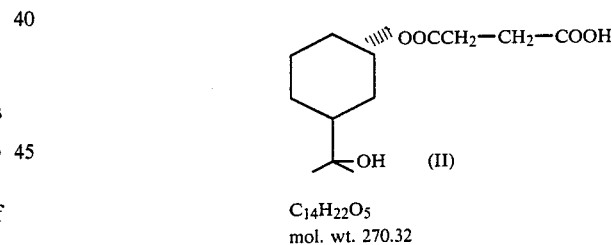

$C_{14}H_{22}O_5$
mol. wt. 270.32

The reaction is carried out, in an optimum way, in an aprotic solvent such as, for example, tetrahydrofuran, dioxane, anhydrousmethylene chloride free from ethanol, catalyzed by dimethylamino-pyridine(D.M. A.P.). Temperature is kept within the range from 20 to 25° C. over a time of 8 to 20 hours, preferably for about 12 hours.

Then, the temperature is taken to reflux (65–66° C.) and kept there for 2 to 5 hours, preferably 3 hours. The so obtained crystalline acid product is redissolved, by adding the same to an equivalent solution of erythromycin base in methylene chloride. The salt (I) which forms is precipitated with isopropyl ether after concentration.

The process according to this invention is illustrated in the following examples, which, however, are not limiting the same.

EXAMPLE 5-(3-carboxy-1-oxopropxy)-α, α 4-trimethyl-3-cyclohexene1-methanol acid (II) (see the reaction scheme above).

A mixtureof 17g (0.1 mole) of d,1-trans-sobrerol, 200 ml. of tetrahydrofuran, 11 g (0.11 mole) of succinic anhydride and 3g (0.025 mole) of 4-dimethylaminopyridine (mol.wt. 122.17) as a catalyst, is left under stirring during 12 hours at room temperature and then is refluxed 3 hours (66° C.). The reaction mixture is then poured into 400 ml of aqueous 5% sulphuric acid solution, leaving under stirring for 1 hour and then is extracted with ethyl acetate (3×300 ml). The combined organic phases are washed with water (3×100 ml) and dried by anhydrous Mg SO$_4$. The solvent is concentrated, under reduced pressure, to a volume of about 100 ml and it is cooled in ice-water. There is filtered under vacuum thereby obtaining, after drying, 24.3 g of a white crystalline product, m.p. 123-125° C.

Theoretic yield=90%.

EXAMPLE 2

Erythromycinsalt of 5-(3-carboxy-1-oxopropoxy)-α, α 4-trimethyl-3-cyclohexene-1-methanol ( I)

Erythromycin base
$C_{37}H_{67}NO_{13}$ +
mol. wt. 733.92
(III)

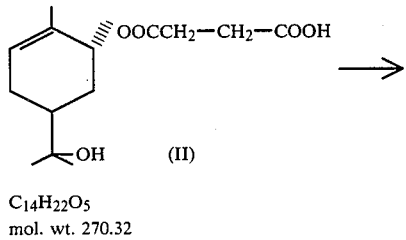

$C_{14}H_{22}O_5$
mol. wt. 270.32

Erythromycin salt
$C_{51}H_{89}O_{18}$
mol. wt. 1004.24
(I)

To a solution of 50 g (0.068 mole) of erythromycin base in 600 ml of methylene chloride, 18.4 g (0.068 mole) of 5-(3-carboxy-1-oxopropoxy)-α, α 4-trimethyl-3-cyclohexene-1-methanol acid is added. The mixture is left under stirring ½ hour (clear solution). 1 liter of isopropyl either is added and the solution is concentrated to a volume of about 800 ml. The solution is cooled in ice-water and is filtered under reduced pressure, to obtain the white, crystalline erythromycin salt.

Yield=g.65 (95% of theoretical) m.p.=80-100° C. Analytical characterization of the compound of formula (II)

1. Elemental analysis for $C_{14}H_{22}O_5$, mol. wt. 270.328 Calculated, % C=62.21,H=8.2,O=29.59; Found, % C=62.44,H=8.14.(Average of 3 tests)

2 I.R. spectrum ( nujol dispersion;cm$^{-1}$) 3415 γ OH; 2320-2880 γ OH acid (several little bands);

1725 C=O ester and acid; 1710; 1320-1208;1155 and 918; (characteristic bands).

3. H$^1$ N.M.R. spectrum (CD Cl$_3$ solvent; internal reference T.M.S. δ p.p.m.); 5.67 centre c.a. (1H=CH); 5.22 centre, c.a. (1H; W$_\frac{1}{2}$=8 Hz; CHOCO); 2.62 b.s. (4H;OC—CH$_2$-CH$_2$—CO); 2.5+1,3 c.a. (5H;=C—CH$_2$—CH—CH/ $_2$—CO) 1.68 b.s. (3H;=C—CH$_3$); 1.2 and 1.12 s. (3H each, gem. CH$_3$).

Legend :
c.a.=complex absorption,
b.s.=broadened singlet
s.=singlet
T.M.S.=tetramethylsilane
W$_\frac{1}{2}$=broadness at half height 4. Mass spectrum (quadrupole, direct insertion, 80 eV, 70 mA; m/z); 252 (M-18)+; 0.56%) 170 (5%); 152 (42%); 137 (19); 134(10); 119 (59); 109 (89); 94(68); 93 (46); 79(0.9); 59 (base peak).

Characterization of the compound of formula (I)

Elemental analysis for $C_{51}H_{89}NO_{18}$, mol.wt. 1004.273.

Calculated, % C=61.00,H=8.93,N=1.39,O=28.63-;Found,% C=61.19,H=8.86,N=1.31.(Average of 3 tests).

2. I.R. spectrum (nujol dispersion, cm$^{-1}$) 3470 γ OH (broadened), 1723 γ CO (ester, lactone, ketone group), 1585 γ as COO⁻, 1165 and 1012 characteristic bands.

3. H$^1$ N.M.R. spectrum(CDCl$_3$solvent; internal reference T.M.S.; δ p.p.m.). 6.68 centre b.s. (1H;=CH); 2.22 centre b.s. (1H W$_\frac{1}{2}$=8Hz; CHOCO terpene fraction); 3.27 s. (3H; CH$_3$—0); 2.57 and 2.53 s. (4H and 6H; O—CO—CH$_2$—CH$_2$—CO and N$^{30}$ (CH$_3$)$_2$; 1.67b.s. (3H; CH$_3$—C=).

Legend : see N.M.R. spectrum above.

ACUTE TOXICITY

Method for studying LD$_{50}$ in the mouse after a single oral administration.

Groups of 10 Swiss albine, female, adult (g.20-22) mice, fasting from the evening preceding the test, are treated by oral way with various doses (4 to 5) of the test drugs, dissolved/suspended in 1% hydroxyethyl cellulose (volume administered : 20ml/kg). Thereafter, the animals are fed again. (Morini MIL fodder for mice)

The 50% lethal dose (LD$_{50}$) is calculated by the method of Litchfield, J.T. and Wilcoxon, F. (J. Pharmacol. 96,99-113,1949) by the mortality data as obtained at 14th day after the drug treatment.

TABLE No. 1

| Acute toxicity in the mouse after oral administration | |
|---|---|
| Substance | DL$_{50}$ in mg/kg |
| CO/1311 | 4322.3 |
| d,l-trans-sobrerol | 2340 |
| erythromycin base | >5000 |

BRONCHOSECRETAGOGUE ACTIVITY

Method of mucoproduction in the rabbit according to Scuri R. et al, Boll Chim. Farm. 119, 181-7, 1980.

Male brown rabbits weighing 2.8-3.5 kg. are employed. To said animals, by surgical operation under anaesthesia, a T shaped tracheal cannula is applied, as described in the bibliographic reference mentioned above.

To the cannula, a container (a polyproylene 2 ml test tube) is applied for periodical collection of the bronchial secretion. The study of mucoproduction started at the fourth day after the operation, is divided into two 4 hour periods for collecting and measuring the mucus, and exactly from 8:30 to 12:30 (I) and from 12:30 to 16:30 (II).

The activity of each drug is tested by administering the same by oesophageal way (os) at the begining of the II period and by evaluating the percent increase of mucoproduction (weight of the mucus as collected) over the II period as compared to the I period.

TABLE No. 2

Bronchosecretague activity in the rabbit. Oral drug administration

| Substance | Activity |
|---|---|
| CO/1311* | 140 |
| d,l-trans-sobrerol | 100 |
| erythromycin | 0 |

The activity of the compound of formula (I), of the present invention, is based on the d,1-trans-sobrerol one, taken equal to 100.

FLUIDIZING "IN VIVO" ACTIVITY

A method for studying viscosity of bronchial mucus of a bronchitic rabbit (R. Scuri et al-Il Farmaco, Ed.Pr. 36, 36–48, 1981).

Male rabbits weighing 27–3.5 kg, made bronchitic by sulphuric acid aerosol treatment according to the method of Cantarelli (G. Cantarelli et al—Il Farmaco, Ed. Pr. 34, 393–416, 1979), are treated with the test drugs and the bronchial mucus is collected by means of a tracheal cannula according to the procedure of R. Scuri (R. Scuri et al -Boll. Chim. Farm. 119, 181–7, 1980). Viscosity of the mucus as withdrawn is studied by using a Contraves RM16 micro viscosimeter and it is recorded by a Rheomat 15T -FC apparatus.

TABLE No. 3

Fluidizing "in vivo" activity of bronchial mucus of bronchitic rabbits. Oral drug administration.

| Substance | Activity |
|---|---|
| CO/1311* | 132 |
| d,l-trans-sobrerol | 100 |
| erythromycin | 0 |

The activity of the compound of formula (I) of this invention is based on the one of d,1-sobrerol, taken equal to 100.

ANTIMICROBIC ACTIVITY

Microbiologic "in vitro" tests. Tests carried out in order to evaluate the values of the Minimum Inhibiting Concentrations (MIC) are performed by the method of the substrate treated with scalar drugs concentrations, by the "multi-points inoculator" technique.

As test strains, bacteria from clinical isolation and from international culture collections are tested.

In the tables, the MIC values (mcg/ml), as obtained employing the Mueller-Hinton medium, are reported.

The MIC values in the tables refer to readings after 24 and 48 hours at 37° C.

TABLE No. 4

| Test strains | Antimicrobic "in vitro" activity | | | |
|---|---|---|---|---|
| | CO/1311 | | erythromycin | |
| 1 Staph. aureus 14154 | 10 | 10 | 10 | 10 |
| 2 Staph. aureus 6538 | 10 | 10 | 10 | 10 |
| 3 Staph. aureus clin | — | — | — | — |
| 4 Staph. epiderm clin | 10 | 10 | 10 | 10 |
| 5 Staph. epiderm clin | −0.1 | −0.1 | −0.1 | −0.1 |
| 6 Microc. luteus 9341 | −0.1 | −0.1 | −0.1 | −0.1 |
| 7 Strept. faecalis 8043 | 0.3 | 0.3 | 0.3 | 0.3 |
| 8 Strept. faecalis clin | 0.4 | 0.4 | 0.3 | 0.3 |
| 9 Bac. subtilis 6633 | — | — | — | — |
| 10 Pseud. aerug. clin | +100 | | +100 | |
| 11 Pseud. aerug. clin | 100 | 100 | 100 | 100 |
| 12 Pseud. aerug. clin | +100 | | +100 | |
| 13 Esch. coli 418 | 25 | 25 | 25 | 25 |
| 14 Serr. marcescens clin | 50 | 50 | 45 | 50 |
| 15 Proteus vulg. X 19 | 2.5 | 2.5 | 2.5 | 2.5 |
| 16 Cand. albicans clin | 100 | 100 | 100 | 100 |

Legend:
+ = greater than
− = smaller than
clin = clinic isolation
The strains with 4 figures are of ATCC.

Pharmacocinetics

Two groups of Wistar rats (180–270g.) are utilized. To the first group the compound of formula (I) of this invention, orally (transoesophageal intubation) at the dose of 800mg/kg, is administered, whilst to the second, again by the oral way, 585 mg/kg of erythromycin are administered.

Before treatment the rats were fasting for about 15 hours and were allowed to drink ad libitum. In both cases at 0.5 h; 1h;1.5 h; 2h; 3h;.4h; 6h from administration 5 rats/time are sacrificed. The blood as collected in test tubes containing sodium heparin is centrifuged and the plasma so obtained is utilized for the quantitative analysis of erythromycin by means of the micorbiologic standard method, using Staphylococcus aureus as a test organisum (P.G. Welling and W.A. Craig, J. Pharm. Sci. 67, 1057 (1978)).

The plasmatic levels rates in erythromycin so measured are significantly higher after a single administration of CO/1311 than the ones which are found after an equidose erythromycin administration.

From the same rats, in similar manner, the lungs are withdrawn and, after homogenizing the tissue, the erythromycin rates are evaluated. The erythromycin rates appear significantly higher following administration of the compound of formula (I) of the present invention.

These tests show an improved bioavailability of the erythromycin administered as CO/1311, compared with that of the antibiotic administered as such. Further, the higher erythromycin rates which are found at the pulmunary level indicate a specific action of the terpenoid moiety of CO/1311 to help theerythromycin tropism toward the pulmonary structures.

In respect to the activity carried on by the compound of this invention as a mucosecretolytion fluidizing-antibiotic agent, the present invention also provides pharmaceutical compositions which contain the compound of the invention in dosage units.

The pharmaceutical forms containing the above mentioned active constituent are preferably those suitable for oral and rectal administration, in particular : capsules, coated tablets, granulate for extemporaneous suspension, little bags and suppositories.

As excipients there may be employed, for the pharmaceutical oral forms : starch, lactose, microgranular cellulose, hydroxypropyl-methylcellulose, sorbitol and more generally diluent, bonding, lubricant, aromatizing, coating, taste masking and edulcorating agents.

For the suppository form there are used as excipients triglycerides of saturated fatty acids, lecithins or phospholipids of more usual pharmaceutical employment.

I claim:

1. Erythromycin salt of 5-(3-carboxy-1-oxopropoxy)-α, α4-trimethyl-3-cyclohexene-1-methanol of formula:

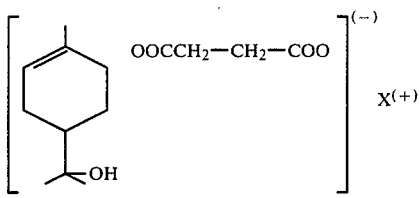

in which $X^{(+)}$ represents the monovalent cation of erythromycin.

2. A pharmaceutical composition having mucosecretolytic-fluidizing and antibody characterized in that it comprises a mucosecretolytic-fluidizing and antibiotic activity effective amount of the compound of formula (I) of claim 1 and at least one pharmaceutically acceptable vehicle or excipient.

3. A method of imparting a mucosecretolytic-fluidizing and antibiotic effect in a host in need thereof characterized in that it comprises administering to said host a mucosecretolytic-fluidizing and antibiotic effective amount of the compound of formula (I) of claim 1.

* * * * *